United States Patent
Gershwin et al.

(10) Patent No.: US 7,244,580 B2
(45) Date of Patent: Jul. 17, 2007

(54) EPSILON IMMUNOGLOBULIN CHAIN DERIVED PEPTIDES FOR INDUCTION OF ANTI-IGE ANTIBODIES

(75) Inventors: Laurel J. Gershwin, Davis, CA (US); Howard David Pettigrew, Burlington, VT (US); Warren V. Kalina, Woodland, CA (US)

(73) Assignee: The Regents of the University of California, Oakland, CA (US)

( * ) Notice: Subject to any disclaimer, the term of this patent is extended or adjusted under 35 U.S.C. 154(b) by 748 days.

(21) Appl. No.: 10/052,788

(22) Filed: Nov. 8, 2001

(65) Prior Publication Data

US 2003/0087314 A1 May 8, 2003

(51) Int. Cl.
- G01N 33/53 (2006.01)
- G01N 33/534 (2006.01)
- G01N 33/535 (2006.01)
- G01N 33/543 (2006.01)
- A61K 39/395 (2006.01)
- C07K 16/06 (2006.01)
- C07K 16/42 (2006.01)
- C12N 5/20 (2006.01)

(52) U.S. Cl. ............. 435/7.95; 435/7.1; 435/7.5; 435/7.94; 435/69.3; 435/70.21; 435/452; 435/975; 436/513; 436/518; 436/547; 436/548; 530/387.9; 530/388.25; 530/389.3; 530/391.3

(58) Field of Classification Search ............ 530/387.9, 530/388.25, 389.3, 391.3; 435/69.3, 70.21, 435/452, 975, 7.1, 7.5, 7.94, 7.95; 436/547, 436/548, 513, 518
See application file for complete search history.

(56) References Cited

U.S. PATENT DOCUMENTS

| 5,583,005 A | 12/1996 | Nishimura et al. |
| 5,629,415 A | 5/1997 | Hollis et al. |

FOREIGN PATENT DOCUMENTS

EP 0044710 * 1/1982

OTHER PUBLICATIONS

Halliwell and Hines, "Studies on equine recurrent uveitis. I: Levels of immunoglobulin and albumin in the aqueous humor of horses with and without intraocular disease", *Current Eye Research*, 4:1023-1031 (1985).
Marti, E. et al., "Partial sequence of the equine immunoglobulin epsilon heavy chain cDNA" *Journal of Veterinary Immunology and Immunopathology*, 47:363-367 (1995).
Marti, E. et al., "Chicken antibodies to a recombinant fragment of the equine immunoglobulin epsilon heavy-chain recognising native horse IgE," *Veterinary Immunology and Immunopathology*, 59:253-270 (1997).
Navarro, P. et al., "The Complete cDNA and Deduced Amino Acid Sequence of Equine IgE," *Journal of Molecular Immunology*, 32:1-8 (1995).
Watson, J.L. et al., "Isolation and Partial Expresion of a cDNA Clone Encoding Equine IgE Heavy Chain and Production of Polyclonal Antibodies to the Recombinant Protein," *Veterinary Allergy and Clinical Immunology*, 5:135-142 (1997).
Watson, J.L. et al., "Phenotypic Characterization of Lymphocyte Subpopulations in Horses Affected with Chronic Obstructive Pulmonary Disease and in Normal Controls," *Vet. Pathol.* 34:108-116 (1997).
Griot-Wenk, M.E. et al., "Partial sequences of feline and caprine immunoglobulin epsilon heavy chain cDNA and comparative binding studies of recombinant IgE fragment-specific antibodies across different species," *Journal of Veterinary Immunology and Immunopathology*, 75:59-69 (2000).

* cited by examiner

*Primary Examiner*—Long V. Le
*Assistant Examiner*—James L. Grun
(74) *Attorney, Agent, or Firm*—Townsend and Townsend and Crew, LLP (57) ABSTRACT

The present invention relates to identification of polypeptides useful for generating antibodies specific for non-human IgE, particularly equine IgE. The invention, therefore, also relates to antibodies that specifically bind to IgE and methods to detect IgE using the antibodies. The invention also provides a kit for detection of IgE.

24 Claims, 1 Drawing Sheet

Figure 1

EPSILON IMMUNOGLOBULIN CHAIN DERIVED PEPTIDES FOR INDUCTION OF ANTI-IGE ANTIBODIES

STATEMENT AS TO RIGHTS TO INVENTIONS MADE UNDER FEDERALLY SPONSORED RESEARCH AND DEVELOPMENT

Not applicable.

BACKGROUND OF THE INVENTION

Allergic diseases are frequently seen in non-human mammalian patients, just as they are in humans. For example, equine allergy most often manifests either as cutaneous or respiratory disease. Urticaria (hives), while not life threatening, is a major cause of economic loss in the horse industry, due not only to treatment expenses, but also to the result of lost activity for show and race horses. Allergy that manifests as respiratory disease varies from rhinitis and bronchitis to chronic obstructive pulmonary disease (heaves) and systemic anaphylactic shock, the latter of which can be fatal. The lack of availability of reliable in vitro methods to detect the allergens causing disease in an individual patient has made diagnosis and treatment of allergic diseases in non-human mammals difficult.

Equine IgE has been studied by several investigators using an assay based on a polyclonal anti-IgE antibody. Halliwell reported that normal horses have 107 µg/ml of serum IgE, which is several times more than normal levels in humans (Halliwell R. E. and Hines, M. T., *Eye Research*, 4:1023-1031 (1985)). Such high levels of equine IgE are likely to be a result of multiple internal parasitic infections. These levels are not unlike those reported for the dog, a genus that is also commonly infested with gastrointestinal parasites (Halliwell R. E. W., *Journal of Immunology*, 110: 422-430 (1973); Halliwell R. E. and Hines, M. T., *Eye Research*, 4:1023-1031 (1985); Swiderski, C. E., *Veterinary Clinics of North America: Equine Practice*, 16:131-151 (2000)).

Recently, the complete nucleotide and deduced amino acid sequence of IgE has been ascertained (Marti, E. et al., *Journal of Veterinary Immunology and Immunopathology*, 47:363-367 (1995); Navarro, P. et al., *Journal of Molecular Immunology*, 32:1-8 (1995); Watson, J. L. et al., *Veterinary Allergy and Clinical Immunology*, 5:135-142 (1997)). As a result of these studies, recombinant fusion proteins, corresponding to equine IgE heavy chain region CH3 and CH4, have been produced that react to equine IgE under various conditions (Marti, E. et al., *Veterinary Immunology and Immunopathology*, 59:253-270 (1997); Watson, J. L. et al., *Veterinary Allergy and Clinical Immunology*, 5:135-142 (1997)). However, conformational requirements such as natural folding of fusion proteins have made it difficult to generate polyclonal and monoclonal antibodies that recognize native equine IgE (Grioto-Wenk, M. E. et al., *Journal of Veterinary Immunology and Immunopathology*, 75:59-69 (2000)). A recombinant fusion protein consisting of parts of CH3 and CH4 has been used to raise polyclonal rabbit antibodies specific for equine IgE (Watson, J. L. et al., *Veterinary Allergy and Clinical Immunology*, 5:135-142 (1997)). However, the antiserum was able to recognize only the reduced/denatured and non-reduced/denatured IgE but not the native IgE. A similar protocol was used by Marti et. al with the use of recombinant fusion protein immunized chickens (Marti, E. et al., *Veterinary Immunology and Immunopathology*, 59:253-270 (1997)).

Due to the very low concentration of IgE in serum, purification of sufficient IgE for production of diagnostic reagents is difficult. Efficient and cost-effective methods for producing antibodies specific to IgE are lacking in the prior art. The present invention addresses these and other needs.

BRIEF SUMMARY OF THE INVENTION

The present invention relates to identification of polypeptides useful for generating antibodies specific for non-human IgE, particularly equine IgE. The invention, therefore, also relates to antibodies that specifically bind to IgE. The invention provides methods to make antibodies that specifically bind to IgE. The invention also provides methods to detect IgE using the antibodies. The invention also provides a kit for detection of IgE.

The present invention relates to an immunogenic composition that induces production of an antibody that specifically binds to equine IgE. The immunogenic composition comprises a polypeptide that is at least 80% identical to SEQ ID NO:1, SEQ ID NO:2, SEQ ID NO:3, SEQ ID NO:4, SEQ ID NO:5, or SEQ ID NO:6.

In one embodiment, the composition includes a carrier molecule. In another embodiment, the composition includes an adjuvant.

In one aspect, the invention comprises an antibody that specifically binds to a polypeptide at least 80% identical to SEQ ID NO:1, SEQ ID NO:2, SEQ ID NO:3, SEQ ID NO:4, SEQ ID NO:5, or SEQ ID NO:6. In a further embodiment, the antibody is an antiserum.

In one aspect the antibody is labeled. The label can be an enzyme, a radiolabel, or biotin.

In one embodiment, the invention is an antibody made by the process of immunizing an animal with a polypeptide at least 80% identical to SEQ ID NO:1, SEQ ID NO:2, SEQ ID NO:3, SEQ ID NO:4, SEQ ID NO:5, or SEQ ID NO:6.

In another embodiment, the invention is a method of making an antibody that specifically binds to equine IgE. The method involves immunizing an animal with an isolated polypeptide, wherein the amino acid sequence of the polypeptide is at least 80% identical to SEQ ID NO:1, SEQ ID NO:2, SEQ ID NO:3, SEQ ID NO:4, SEQ ID NO:5, or SEQ ID NO:6; and then collecting antiserum from the animal.

In another aspect, a carrier molecule is injected with the polypeptide. In a further aspect, an adjuvant is injected with the polypeptide.

In one embodiment, the present invention provides a method of detecting equine immunoglobulin E protein in a biological sample. The method includes contacting the sample with the equine IgE antibody, forming an antigen/antibody complex; and detecting the presence or absence of the antigen/antibody complex.

In one aspect, the IgE antibody is immobilized on a solid surface. In another aspect the antigen is immobilized on a solid surface.

In a further aspect, the complex is detected by using a second labeled antibody.

In one aspect, the IgE antibody is labeled so that the antigen/antibody complex can be detected. The label can be an enzyme, a radiolabel, or biotin. The biological sample can be horse serum or other horse tissue.

In one embodiment the present invention provides a kit for detection of equine immunoglobulin E protein in a biological sample. The kit includes an antibody directed against equine IgE and a method for detecting specific binding of the equine IgE antibody to equine IgE.

BRIEF DESCRIPTION OF THE DRAWINGS

FIG. 1: FIG. 1 shows the results of an assay for IgE in horses with clinical signs of allergy. Serum samples were taken from 64 horses with clinical allergy symptoms. ELISA assays were performed after pre-treating ninety-six well plates with a panel of potential allergens. After incubation of the allergens with horse serum, affinity-purified anti-P5 antiserum was added. Labeled secondary antibodies were used to detect the amount of IgE in the sample. Results are based on a comparison to ELISA's done with serum from non-allergic horses. Individual bars of FIG. 1 represent a single allergen. The vertical axis shows the number of horses positive for that allergen.

DETAILED DESCRIPTION OF THE INVENTION

I. Introduction

Allergy is the term commonly used to describe a type 1 hypersensitivity reaction, mediated by IgE antibodies. Such a reaction is initiated by allergic stimulation of cytokine production by T helper cells (Th2) that make cytokines IL-4 and IL-13, which are stimulatory for IgE production. Once produced by plasma cells IgE binds tightly to blood basophils and tissue mast cells. This accounts for its short half life in serum (12 hours to 2.5 days) (Hirano, T. et al., *International Archives of Allergy and Applied Immunology*, 71:182 (1983); Nielsen, K. et al., *Immunology*, 35:811-6 (1978); Patterson, R. et al., *American Journal of Medicine*, 58:553-8 (1975)). Upon re-exposure to allergen via inhalation, ingestion, or topical application, IgE molecules on mast cells are cross-linked, causing the cells to release/produce a variety of potent mediators, with activity on vasculature and smooth muscle. Clinical signs of allergic disease are a direct result of this mediator release.

Allergy is most well characterized in humans. Certain "atopic" individuals are prone to strong immediate hypersensitivity responses and are said to suffer from allergies. Symptoms of allergy in humans include vascular permeability, vasodilation, bronchial and visceral smooth muscle contraction and local inflammation. In its most extreme form, allergy can cause anaphylaxis and result in death.

Like humans, non-human mammals also suffer from allergic diseases. As in the human model of allergic disease, atopic mammals have elevated levels of IgE in serum. Detection of IgE in serum is thus a useful tool in diagnosis of allergy in these animals. Antibodies against equine IgE would be useful to detect serum levels of the protein. However, it has been unusually difficult to generate antibodies suitable for detection of IgE in biological samples using either full length IgE or IgE fusion proteins.

The present invention is based on the amino acid sequence of the epsilon chain of non-human mammals, using algorithms to predict accessibility, hydrophilicity, and surface probability of particular peptide fragments. These antigenic peptides can easily be synthetically produced with well-known techniques. Small peptides serve as haptens and can be conjugated to large carrier molecules to enhance their immunogenicity. As shown below, the selection of antisera against peptides with reactivity to native proteins offers a more simplified method to the generation of polyclonal antibodies against proteins that are difficult to purify.

II. Definitions

As used herein, the following terms have the meanings ascribed to them unless specified otherwise.

The terms "IgE" or "immunoglobulin E" refer to antibodies that mediate the immediate hypersensitivity reactions that are responsible for the symptoms of hay fever, asthma, hives, and anaphylactic shock.

The terms "immunogen" or "immunogenic composition" refer to a composition that elicits the production of an antibody that binds a component of the composition when administered to an animal, or that elicits the production of a cell-mediated immune response against a component of the composition.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harrow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to IgE protein, polymorphic variants, alleles, orthologs, and conservatively modified variants, or splice variants, or portions thereof, can be selected to obtain only those polyclonal antibodies that are specifically immunoreactive with IgE proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}$P, $^{125}$I, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:3 can be made detectable, e.g., by incorporating a radiolabel into the peptide, and used to detect antibodies specifically reactive with the peptide).

The term "contact" or "contacting" is used herein interchangeably with the following: combined with, added to, mixed with, passed over, incubated with, flowed over, etc.

The term "immunoassay" is an assay that uses an antibody to specifically bind an antigen. The immunoassay is characterized by the use of specific binding properties of a particular antibody to isolate, target, and/or quantify the antigen.

The term "carrier molecule" means an immunogenic molecule containing antigenic determinants recognized by T cells. A carrier molecule can be a protein or can be a lipid. A carrier protein is conjugated to a polypeptide to render the polypeptide immunogenic. Carrier proteins include keyhole limpet hemocyanin, horseshoe crab hemocyanin, and bovine serum albumin.

The term "adjuvant" means a substance that nonspecifically enhances the immune response to an antigen. Adjuvants include Freund's adjuvant, either complete or incomplete; Titermax gold adjuvant; alum; and bacterial LPS.

The terms "protein," "polypeptide," or peptide" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission.

The terms "identical" or percent "identity," in the context of two or more polypeptide sequences, refer to two or more sequences or subsequences that are the same or have a specified percentage of amino acid residues that are the same (i.e., 60% identity, preferably 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." Preferably, the identity exists over a region that is 15 amino acids in length.

When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., J. Mol. Biol. 215:403-410 (1990), respectively. BLAST and BLAST 2.0 are used, with the parameters described herein, to determine percent sequence identity for the peptides of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a wordlength of 3, and expectation (B) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between amino acid sequences would occur by chance.

An indication that two polypeptides are substantially identical is that the first polypeptide is immunologically cross reactive with the antibodies raised against the second polypeptide. Thus, a polypeptide is typically substantially identical to a second polypeptide, for example, where the two peptides differ only by conservative substitutions.

The terms "isolated or purified" refer to material that is substantially or essentially free from components that normally accompany it as found in its native state. Purity and homogeneity are typically determined using analytical chemistry techniques such as polyacrylamide gel electrophoresis or high, performance liquid chromatography. A protein that is the predominant species present in a preparation is substantially purified. The term "purified" denotes that a protein gives rise to essentially one band in an electrophoretic gel. Particularly, it means that the protein is at least 85% pure, more preferably at least 95% pure, and most preferably at least 99% pure.

"Biological sample" refers to any sample obtained from a living or dead organism. Examples of biological samples include biological fluids and tissue specimens.

The terms "serum" and "antiserum" are used interchangeably and refer to the fluid portion of the blood, free of cells and clotting factors.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three-dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., phosphatase domains, ligand binding domains, etc. Typical domains are made up of sections of lesser organization such as stretches of β-sheet and α-helices. "Tertiary structure" refers to the complete three-dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

III. Generation of Antigenic Peptides from IgE Protein

According to the present invention, algorithms are used to analyze the entire amino acid sequence of a non-human mammalian IgE protein and predict accessible epitopes. The algorithms predict hydrophilicity, surface probability and accessibility, flexibility), antigenicity and secondary structure (Chou, P. Y. and Fasman, G. D, *Annual Review of Biochemistry*, 47:251-76 (1978), Hopp, T. P. and Woods, K. R. *Proceedings of the National Academy of Sciences*, 78:3824-8, (1981), Kyte, J. and Doolittle, R. F. *Journal of Molecular Biology*, 157:105-32 (1982), Hopp, T. P. and Woods, K. R., *Molecular Immunology*, 20:483-9 (1983), Jameson, B. A. and Wolf, H., *CABIOS*, 4:181-6 (1988), Karplus, P. A. and Schultz, G. E., *Naturwissenschaften*, 72:712-3 (1985)).

The typical size of a peptide antigen of the invention is between 10 and 15 amino acids. Peptides as small as six amino acids or as large as twenty amino acids can be used to generate anti-peptide antibodies.

As shown below, these methods can be used to identify equine IgE peptides of the invention. The same approach is conveniently useful for identifying antigenic peptides of any IgE molecule for which amino acid sequence data is available. The method can be used to identify antigenic IgE amino peptides from, for example, cattle, cats, sheep, and the like. In addition, simply comparing the equine IgE sequence to that of other species can be used to identify antigenic IgE peptides in homologous IgE proteins.

Methods of generating adequate quantities of peptides for generating antibodies are known to those of skill in the art. Peptide synthesis is routinely carried out using automated solid-phase synthesizers. Alternatively, peptides may be ordered from commercial suppliers.

IV. Generation of Antibodies Specific for IgE

Methods of producing polyclonal and monoclonal antibodies that react specifically with a desired protein are known to those of skill in the art (see, e.g., Coligan, *Current Protocols in Immunology* (1991); Harlow & Lane, *Antibodies: A Laboratory Manual* (1988). Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

Peptides are chemically coupled to carrier proteins before being used as an immunogen. Ideal attributes of carrier proteins include antigenicity and solubility. MBS (m-maleimidobenzoyl-N-hydroxysuccinimide ester) cross links amino- and carboxyyl-terminal thiol groups in the peptide with lysine side chains present in the carrier protein. Commercially available kits are useful for conjugating peptides to carrier proteins.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra). In the case of antibodies directed against a peptide coupled to a carrier protein, it is desirable to purify the antisera further using immunoaffinity chromatography on carrier protein-Sepharose. Alternatively, peptide-Sepharose may be used to purify the antisera.

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-equine IgE proteins using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better.

V. Detection of IgE

The IgE antibodies of the invention can be detected and/or quantified using any of a number of well-recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case IgE or an antigenic subsequence thereof). The antibody (e.g., anti-IgE) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled IgE polypeptide or a labeled anti-IgE antibody. Alternatively, the labeling agent may be a third moiety, such a secondary antibody, which specifically binds to the antibody/IgE complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting the IgE protein in samples may be either competitive or noncompetitive. Noncompetitive immunoassays are assays in which the amount of antigen is directly measured. In one preferred "sandwich" assay, for example, the anti-IgE antibodies can be bound directly to a solid substrate on which they are immobilized. These immobilized antibodies then capture IgE protein present in the test sample. The IgE polypeptides are thus immobilized and then bound by a labeling agent, such as a second IgE antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the IgE protein present in the sample is measured indirectly by measuring the amount of known, added (exogenous) IgE protein displaced (competed away) from an anti-IgE antibody by the unknown IgE present in a sample. In one competitive assay, a known amount of the IgE protein is added to a sample and the sample is then contacted with an antibody that specifically binds to the IgE protein. The amount of exogenous IgE protein bound to the antibody is inversely proportional to the concentration of the IgE protein present in the sample. In a particularly preferred embodiment, the antibody is immobilized on a solid substrate. The amount of IgE protein bound to the antibody may be determined either by measuring the amount of IgE protein present in an IgE/antibody complex, or alternatively by measuring the amount of remaining uncomplexed protein. The amount of IgE may be detected by providing a labeled IgE molecule.

A hapten inhibition assay is another preferred competitive assay. In this assay the known IgE protein is immobilized on a solid substrate. A known amount of anti IgE antibody is added to the sample, and the sample is then contacted with the immobilized IgE. The amount of anti IgE antibody bound to the known immobilized IgE is inversely proportional to the amount of IgE present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Other Assay Formats

Western blot (immunoblot) analysis is used to detect and quantify the presence of the IgE in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind IgE. The anti-IgE antibodies specifically bind to IgE on the solid support. These antibodies may be directly labeled or alternatively may be subsequently detected using labeled antibodies (e.g., labeled sheep anti-mouse antibodies) that specifically bind to the anti IgE antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34-41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize IgE, or secondary antibodies that recognize anti-IgE antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Diagnosis of Allergy in Mammals

Methods to detect allergy in mammals are known to those of skill in the art. See for example, *Immunology* (Kuby, 3$^{rd}$ ed. 1998). With an appropriate antibody directed against an IgE protein, detection of IgE can serve as a diagnostic test for allergy. An elevated serum level of IgE can indicate type one hypersensitivity.

Serum IgE levels can be detected using the radioimmunosorbant test (RIST). This sensitive technique can detect nanogram levels of total IgE. Serum is reacted with agarose beads or paper discs coated with an IgE antibody. After the beads or discs are washed, a second radiolabeled IgE antibody is added. After appropriate washing steps, the amount of bound radiolabeled IgE is measured using a scintillation counter.

A radioallergosorbent test (RAST) detects the serum levels of IgE specific for a given allergen. The allergen is coupled to beads or discs, serum is added, and unbound antibody is washed away. The amount of IgE bound to the allergen is measured by adding $^{125}$I-labeled IgE antibody, washing the beads, and counting the bound radioactivity.

Other immunoassays that detect the presence of IgE may also be used to diagnose allergy in mammals.

VII. Kits for Detecting IgE

The present invention also provides for kits for detecting IgE protein. Such kits can be prepared from readily available materials and reagents. For example, such kits can comprise any one or more of the following materials: unlabeled IgE antibody, a second labeled antibody directed against the IgE antibody, labeled IgE antibody, allergens that bind IgE, IgE protein or peptides for use as controls, solid supports for binding antibody or antigen, appropriate buffer systems, reaction tubes, and instructions for detection of IgE. A wide variety of kits and components can be prepared according to the present invention, depending on the intended user of the kit and the particular needs of the user. For example, the kit can be tailored to measure IgE levels in serum or to determine if a particular antigen is bound to IgE.

EXAMPLES

The following examples are provided by way of illustration only and not by way of limitation. Those of skill in the art will readily recognize a variety of noncritical parameters that could be changed or modified to yield essentially similar results.

Example 1

Generation and Characterization of Antibodies Specific for Equine IgE

Materials and Methods

Selection of Peptides: The entire amino acid sequence of equine IgE, based on the predicted 566 translated amino acids, was used to generate algorithms to predict accessible epitopes. The algorithms combine the Hopp and Woods hydrophilicity scale, surface probability and accessibility scales, Karplus and Schulz flexibility scale, and Jameson-Wolf antigenic index. Chou and Fasman algorithms were used to determine secondary structure including turns, alpha helices, and beta sheets. Based on data obtained from the above algorithms, six 15 amino acid length peptides were selected for synthesis. The following is a list of the chosen peptides and their location on the epsilon heavy chain: P1 (VTYKRHDLLRTRPRK; SEQ ID NO:1) end portion of C2, P2 (RTRPRKCTESEPRGV; SEQ ID NO:2) end portion of C2, P3 (LAACCKDTKTTNITL; SEQ ID NO:3) beginning of C1, P4 (IQTDQQATTRPKSQW; SEQ ID NO:4) early portion of C4, P5 (LIDGQKVDEQFPQHG; SEQ ID NO:5) middle portion of C2, P6 (RVVASGKWAKQKFTC; SEQ ID NO:6) latter portion of C1. All peptides were manufactured by Sigma Genosys, purified by HPLC, and provided as lyophilized powder.

Conjugation of Peptides to Keyhole Limpet Hemocyanin (KLH): Each individual peptide was conjugated, via carboxyl groups, to KLH with the use of an Imject Immunogen EDC Conjugation Kit with mcKLH (Pierce, 77602). Approximately 2 mg of peptide was conjugated to 2 mg of KLH by the carbodiimide EDC in 0.1 M MES, 0.9M NaCl, pH 4.7 for 2 hours. Removal of residual EDTA from the hapten-carrier mixture was accomplished by a gel filtration column of cross-linked dextran (Pierce).

Immunization of Rabbits with Peptide-Carrier Conjugates: Eleven male and female New Zealand white rabbits were immunized separately with each peptide-carrier conjugate. To ascertain the most efficient adjuvant, six rabbits were immunized with 500 µg of peptides 1-6 in Freund's complete adjuvant (Gibco, 15721-030). Rabbits received booster immunizations with 250 µg peptides 1-6 at three week intervals for a total of 3 boosts in Freund's incomplete adjuvant (Gibco, 15720-030). The five other rabbits were immunized with Titermax gold adjuvant (Sigma, T-2684) in the same manner (P6 was not included). Three weeks after the third booster immunization, each rabbit was bled and the serum was stored for future use.

Peptide Specific ELISA: An Enzyme Linked Immunosorbant Assay (ELISA) was performed to measure antibodies in antiserum that were specific to unconjugated peptides or peptides conjugated to ovalbumin, an irrelevant carrier. Ninety-six well polystyrene plates were sensitized with 1 µg per well of each individual peptide in carbonate-bicarbonate buffer, pH 9.6. Plates were then incubated overnight at 4° C. On the following day, plates were blocked with 1% rabbit serum albumin (Sigma, A-0639) in 1M carbonate bicarbonate buffer, pH 9.6 and incubated at 37° C. for 1 hour. Plates were then soaked with a 0.1% Tween PBS solution and washed vigorously five additional times. Antiserum to the respective peptide was added to each well at various dilutions in PBS and incubated for 1 hour at 37° C. Plates were washed as before. Secondary goat anti-rabbit IgG(H+L) HRP (Zymed, 65-6120) diluted 1:10,000 was added and incubated for 1 hour at 37° C. Following a final wash, plates were developed with the use of o-phenylenediamine (Sigma, P1526) in 0.1M sodium citrate, pH 4.5. After 200 µl of substrate was added to each well, the plates were read on a Molecular Devices spectrophotometer (UVmax Microplate Reader) in dual wavelengths 450 and 650.

Evaluation of Peptide Specific Antiserum using Horse Serum Immunoblot: A 12% lower, 4% upper polyacrylimide gel (PAGE) was cast on a Mini-Protean Electrophoresis apparatus (Biorad). Serum from a horse with clinical history of allergy was diluted 1:1 in reducing PAGE buffer. After completion, proteins were transferred to nitrocellulose with the use of a Mini-Protean Transblotter (Biorad). The nitrocellulose was then cut into strips and placed in 16×125 mm test tubes where they where subsequently blocked for 30 minutes with 3% skim milk (BBL, 11915). Rabbit anti-peptide antiserum was added at various dilutions to each tube and incubated overnight with the addition of 0.002% sodium azide at room temperature. Blots were washed three times with a 0.2% Tween PBS solution. Secondary goat anti-rabbit IgG(H+L) HRP diluted 1:1000 was incubated in the same manner. Blots were washed in the same manner and developed with the use of 4-chloronapthol substrate (Biorad, 170-6534).

Reactivity of Peptide Specific Antiserum in an Ovalbumin Specific Equine IgE ELISA: An antigen-specific ELISA was done in the same manner as the peptide-specific ELISA. Microtiter wells were sensitized with 1 µg of ovalbumin (Sigma, A-5503) and blocked with 0.5% rabbit serum albumin. After an hour of incubation, plates were washed as before. Serum from ovalbumin immunized horses (kindly provided by Dr. David Horohov, School of Veterinary Medicine, Louisiana State University) was added to each ovalbumin-sensitized well at a dilution of 1:4. Pre-ovalbumin immunization sera were used as negative controls and diluted in the same manner. Secondary anti-peptide antisera was used at various dilutions and incubated as described above. Following a brief wash, goat anti-rabbit HRP was added and incubated. After a vigorous wash, plates were developed and read as described above.

Purification of Peptide specific antibodies by Affinity Chromatography: Affinity purification of peptide specific antisera was obtained with the use of EDC/Diaminodipropylamine hmmobilization Kit (Pierce, 44899). Five mg of peptide was conjugated to diaminodipropylamine with the use of EDC according to the manufacture's instructions. Following conjugation each peptide column was equilibrated with PBS pH 7.4. Using 50% saturated ammonium sulfate, five milliliters of hyperimmunized rabbit serum was fractionated, concentrated to 1 milliliter, and dialyzed against PBS. One milliliter of serum was then added to the column and incubated for 1 hour. Following incubation, the column was washed with 15 milliliters of PBS and eluted with 0.1 mM glycine, pH 3.0. In tubes with eluted protein, low pH was neutralized with an equal amount of 10× PBS.

Reactivity of Peptide Specific Antiserum to other Equine Immunoglobulin Isotypes: Serum from a normal horse with no clinical sign of allergy was fractionated three times with 50% saturated amonium sulfate. The sample was then dialyzed against PBS, pH 7.4 using cellulose ester dialysis tubing with a molecular weight cut off of 100 kDa. Each well of a ninety-six well microtiter ELISA plate was sensitized with either 2 μg, 1 μg, 500 ng, or 250 ng of horse immunoglobulins. ELISA assays were performed as described for the peptide-specific ELISA.

Results

Anitibodies Derived against Peptides in ELISA: Each peptide-immunized rabbit produced antisera against the corresponding peptide. Table 1 shows the results of the peptide-specific ELISA. Titers to individual peptides varied, but rabbits made a response only to their respective peptide and carrier. Furthermore, peptide-specific antibody titers were much higher in rabbits immunized with complete Freund's adjuvant as opposed to Titermax adjuvant.

TABLE 1

Peptide Specific ELISA.

| Peptide # | OD pre-immune* | OD post-immune* | P/N ratio** |
|---|---|---|---|
| 1 | 0.016 | 0.211 | 13.2 |
| 2 | 0.023 | 0.109 | 4.76 |
| 3 | 0.019 | 0.179 | 9.42 |
| 4 | 0.015 | 0.070 | 4.67 |
| 5 | 0.018 | 0.227 | 12.6 |
| 6 | 0.018 | 0.275 | 15.3 |

*Average optical density read in dual wavelength at 450 nm and 650 nm.
**P/N is a ratio of post value/pre value where P/N = 2.00 is considered positive.

Peptide Derived Antibodies in Equine IgE Immunoblot: Reactivity of peptide-specific antibodies was tested by immunoblot analysis of IgE isolated from allergic horse serum. The IgE was purified first by fractionation with 50% saturated amonium sulfate, followed by size exclusion dialysis using cellulose ester dialysis tubing at 100 kDa molecular weight cut off. Peptide-specific antisera reacted with denatured/reduced equine IgE in an immunoblot assay. All peptides were designed for continuous epitopes, and the peptide-specific antisera recognized continuous, whole heavy chain IgE at 65 kDa. P1, P2 and P3 antisera consistently produced the densest bands in immunoblot. P5-specific antisera reacted to a single 65 kDa band but with less intensity than P1, 2 and 3. P4 and P6 antisera reacted with a band that correlated to the molecular weight of IgE epsilon chain but also with other bands. This result is consistent even after affinity purification. There was no reactivity of secondary antibodies with equine proteins.

Ovalbumin Specific Equine IgE ELISA: To test for reactivity of the antiserum with IgE bound to antigen, serum from ponies with an ovalbumin allergy was used in ELISA. Serum obtained from the ponies before ovalbumin immunization and aerosolization was used as a negative control. Pre-peptide, immune rabbit serum was also used as a negative control. Table 2 shows the data expressed in optical density units and as a ratio of positive to negative signal. P1 and P5 recognized antibody bound to ovalbumin; however, P2, 3, 4, and 6 failed to recognize bound native IgE in this ELISA. In another ELISA (data not shown), P1 antisera reacted strongly to horse immunoglobulins fractionated with saturated ammonium sulfate. The samples had been diluted beyond the point of probable IgE detection. However, anti-P5 sera did not react with the fractionated, diluted samples.

TABLE 2

Ovalbumin Specific IgE ELISA.

| Peptide # | Pre-OVA Serum (O.D.)* | Post-OVA Serum (O.D.)* | P/N Ratio** |
|---|---|---|---|
| 1 | 0.029 | 0.130 | 4.48 |
| 2 | 0.017 | 0.016 | 0.94 |
| 3 | 0.015 | 0.024 | 1.60 |
| 4 | 0.024 | 0.026 | 1.08 |
| 5 | 0.026 | 0.079 | 3.04 |
| 6 | 0.026 | 0.024 | 0.92 |

*Average optical density read in dual wavelength at 450 nm and 650 nm.
**P/N is a ratio of post value/pre value where P/N = 2.00 is considered positive.

Reactivity of Peptide Specific Antiserum to Other Equine Immunoglobulins: Peptide 1 and 2 antiserum showed reactivity to other equine immunoglobulins in ELISA. Both peptide 1 and 2 antiserum produced relatively the same optical densities to horse immunoglobulins as they did to their respective peptide. Furthermore, optical density increased proportionally with equine antibody concentration. In contrast, antiserum specific for peptides 3, 4, 5, and 6 did not show any reactivity with non-IgE immunoglobulins in this ELISA format.

Example 2

Use of Equine IgE Antibodies to Detect IgE Protein in Horses

Materials and Methods

Standardized Allergen Specific Equine IgE ELISA: Sixty-six horses with various clinical signs of allergy were tested in an antigen-specific IgE ELISA against the following seven antigens: mold mix (Greere M03-34-1F4), GS7 grass mix, (P27-40-3F14), western tree mix (P39-1-1F2), grain mill dust mix (D02-22-1X2), mosquito mix (B55-8-1P1), mite mix (B060-73-1C1), and horsefly mix (B43-21-1F4). Allergen-specific ELISA's were performed in the same manner as the ovalbumin-specific ELISA. The rabbit anti-P5 peptide antibody was affinity purified before use. Undiluted serum from each test horse was assayed. The negative control was a pool of horse serum from eight non-allergic horses. Values on the ELISA were recorded as percent of negative control. Anything above 200% is a positive result.

Results

Figure 1:
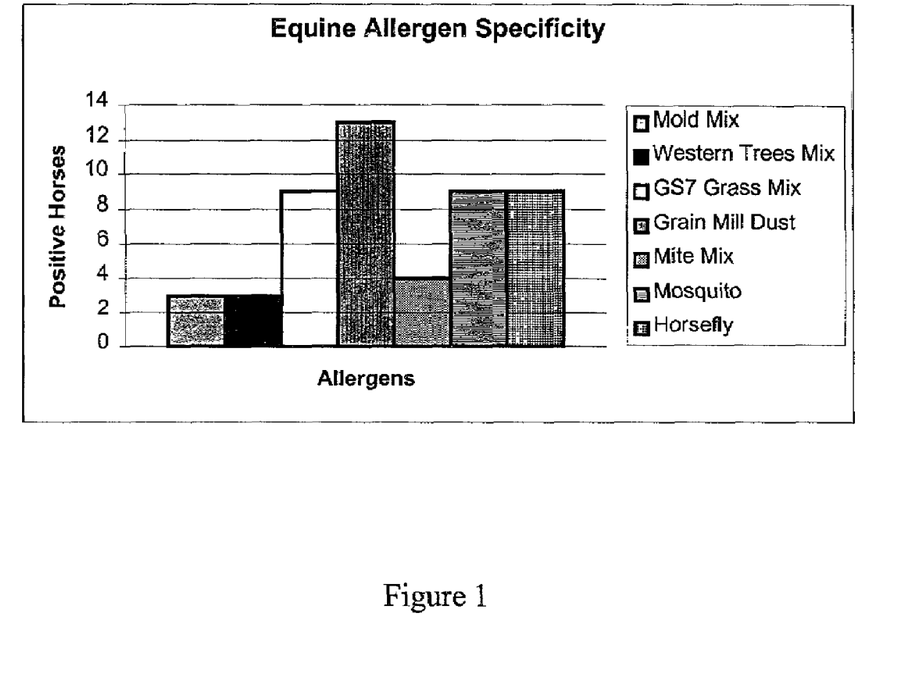

Allergen Specific Equine IgE ELISA: Sixty-four horses, with clinical signs of allergy, were bled by veterinarians throughout the western and Midwestern United States. Serum samples were tested in an allergen-specific IgE ELISA using affinity-purified anti-peptide antibodies. Several common mixes of allergens were used to identify probable allergen sensitivities. Common allergen mixes used were: molds, western pollens, western tree pollens, grain mill dust mix, mite mix, mosquito extract, and horsefly extract. The results of evaluating sera from sixty-four horses are summarized in FIG. 1. Assessment of horses that were positive for any given allergen was based on a comparison with pooled horse serum from eight nonallergic horses. Sample to negative (S/N) ratios were used to determine a reactivity score in the following way: negative reactivity, less than 1.5; borderline reactivity, between 1.50 and 1.99; positive reactivity, between 2.00 and 4.00; and high positive reactivity, greater than 4.00. Fourteen horses showed positive reactivity to grain mill dust. Nine displayed reactivity to grasses, horsefly, and mosquito. Four horses were reactive to mites. Three horses had a positive reaction to molds or western trees.

Grain mill dust was the most common allergen. Of the horses tested for reactivity to grain mill dust allergen, twenty-five horses were borderline, twelve were positive, and two were highly positive.

Severely atopic horses are defined as showing reactivity to at least four of the seven antigens. Four horses displayed positive reactivities to multiple allergens. All atopic horses were positive for reactivity to grain mill dust.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. An isolated or purified antibody that specifically binds to native equine IgE, wherein the isolated or purified antibody specifically binds to a polypeptide consisting of amino acid sequence SEQ ID NO:5.

2. The antibody of claim 1, wherein the antibody is a polyclonal antibody.

3. The antibody of claim 1, wherein the antibody is a monoclonal antibody.

4. A composition comprising an isolated or purified antibody that specifically binds to a polypeptide consisting of SEQ ID NO:5, wherein the antibody specifically binds to native equine IgE.

5. The composition of claim 4, wherein the antibody is a polyclonal antibody.

6. The composition of claim 4, wherein the antibody is a monoclonal antibody.

7. The composition of claim 4, wherein the antibody is labeled.

8. The composition of claim 7, wherein the antibody is labeled with an enzyme that generates a detectable signal.

9. The composition of claim 7, wherein the antibody is labeled with radioactive iodine.

10. The composition of claim 7, wherein the antibody is labeled with biotin.

11. A kit for detection of native equine immunoglobulin E in a biological sample, the kit comprising:
    the composition of claim 4; and
    means for detecting specific binding of said antibody to native equine immunoglobulin E.

12. A method of detecting equine immunoglobulin E protein as antigen in a biological sample, the method comprising:
    contacting the sample with the antibody of claim 1 under conditions suitable for formation of an antigen/antibody complex; and
    detecting presence or absence or level of the antigen/antibody complex as indicative of the presence or absence or level of the equine IgE antigen in the sample.

13. The method of claim 12, wherein the antibody is immobilized on a solid surface.

14. The method of claim 12, wherein the antigen is immobilized on a solid surface.

15. The method of claim 14 wherein the equine IgE antigen is allergen-specific equine IgE and the antigen is immobilized on the solid surface by contacting the sample with at least one allergen immobilized on the solid surface under conditions suitable for formation of an immobilized antigen/allergen complex before the step of contacting with the antibody.

16. The method of claim 12, wherein the antibody is labeled, such that the antigen/antibody complex can be detected.

17. The method of claim 16, wherein the label is an enzyme capable of generating a detectable signal.

18. The method of claim 16, wherein the label is radioactive iodine.

19. The method of claim 16, wherein the label is biotin.

20. The method of claim 16, wherein the biological sample is serum.

21. The method of claim 12, wherein the complex is detected with a second labeled antibody specific for equine IgE or for the antibody.

22. A method of making a polyclonal antibody that specifically binds to native equine IgE, the method comprising:
    immunizing an animal with an immunogenic composition comprising an isolated equine IgE-derived polypeptide consisting of amino acid sequence SEQ ID NO:5; and
    collecting antiserum from the animal.

23. The method of claim 22 wherein the composition includes an adjuvant.

24. The method of claim 22 wherein the composition includes a carrier molecule.

* * * * *

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence:epitope
      peptide P1, end portion of C2 of equine IgE epsilon heavy
      chain

<400> SEQUENCE: 1

Val Thr Tyr Lys Arg His Asp Leu Leu Arg Thr Arg Pro Arg Lys
 1               5                  10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence:epitope
      peptide P2, end portion of C2 of equine IgE epsilon heavy
      chain

<400> SEQUENCE: 2

Arg Thr Arg Pro Arg Lys Cys Thr Glu Ser Glu Pro Arg Gly Val
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence:epitope
      peptide P3, beginning of C1 of equine IgE epsilon heavy
      chain

<400> SEQUENCE: 3

Leu Ala Ala Cys Cys Lys Asp Thr Lys Thr Thr Asn Ile Thr Leu
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence:epitope
      peptide P4, early portion of C4 of equine IgE epsilon
      heavy chain

<400> SEQUENCE: 4

Ile Gln Thr Asp Gln Gln Ala Thr Thr Arg Pro Lys Ser Gln Trp
 1               5                  10                  15

<210> SEQ ID NO 5
```

```
<211> LENGTH: 15
<212> TYPE: PRT
<213> ORGANISM: Artificial Sequence
<220> FEATURE:
<223> OTHER INFORMATION: Description of Artificial Sequence:epitope
      peptide P5, middle portion of C2 of equine IgE epsilon
      heavy chain

<400> SEQUENCE: 5

Leu Ile Asp Gly Gln Lys Val Asp Glu Gln Phe Pro Gln His Gly
  1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:epitope
      peptide P6, latter portion of C1 of equine IgE epsilon
      heavy chain

<400> SEQUENCE: 6

Arg Val Val Ala Ser Gly Lys Trp Ala Lys Gln Lys Phe Thr Cys
  1               5                  10                  15
```